United States Patent
Hawkins

(10) Patent No.: US 11,058,976 B2
(45) Date of Patent: Jul. 13, 2021

(54) VALVE-SENSOR ASSEMBLY

(71) Applicant: Cummins Filtration IP, Inc., Columbus, IN (US)

(72) Inventor: Charles W. Hawkins, Sparta, TN (US)

(73) Assignee: CUMMINS FILTRATION IP, INC., Columbus, IN (US)

( * ) Notice: Subject to any disclaimer, the term of this patent is extended or adjusted under 35 U.S.C. 154(b) by 79 days.

(21) Appl. No.: 16/465,331

(22) PCT Filed: Nov. 9, 2017

(86) PCT No.: PCT/US2017/060781
§ 371 (c)(1),
(2) Date: May 30, 2019

(87) PCT Pub. No.: WO2018/102095
PCT Pub. Date: Jun. 7, 2018

(65) Prior Publication Data
US 2019/0388814 A1    Dec. 26, 2019

Related U.S. Application Data

(60) Provisional application No. 62/429,266, filed on Dec. 2, 2016.

(51) Int. Cl.
*B01D 36/00* (2006.01)
*B01D 35/30* (2006.01)
(Continued)

(52) U.S. Cl.
CPC ........... *B01D 36/005* (2013.01); *B01D 29/21* (2013.01); *B01D 35/301* (2013.01);
(Continued)

(58) Field of Classification Search
CPC .... B01D 36/005; B01D 36/006; B01D 36/00; B01D 29/21; B01D 29/11; B01D 29/35;
(Continued)

(56) References Cited

U.S. PATENT DOCUMENTS

2004/0069694 A1* 4/2004 Gamble ............... B01D 36/005
                                                                    210/85
2005/0167351 A1    8/2005 Herman et al.
(Continued)

FOREIGN PATENT DOCUMENTS

CN          105545551       5/2016
WO      WO 2015/081222      6/2015

OTHER PUBLICATIONS

Chinese Office issued for CN 2017800730468, dated Dec. 5, 2019, with English language translation, 13 pages.
(Continued)

*Primary Examiner* — Robert Clemente
*Assistant Examiner* — Akash K Varma
(74) *Attorney, Agent, or Firm* — Foley & Lardner LLP

(57) ABSTRACT

A valve-sensor assembly for a filter assembly that filters water from a fluid. The valve-sensor assembly includes a sensor body and a drain valve body. The sensor body includes a filter element engagement portion having a hollow interior that extends longitudinally through a length of the sensor body and a protrusion that extends circumferentially along an exterior surface of the filter element engagement portion. The sensor body further includes one or more water-in-fluid sensors provided at the exterior surface of the filter element engagement portion. The drain valve body includes a main body having a drain port, and a valve extending from the main body and extending at least partially within the hollow interior. The valve has an interior passage in fluid communication with the drain port.

21 Claims, 6 Drawing Sheets

(51) Int. Cl.
    *B01D 29/21*     (2006.01)
    *F16K 37/00*     (2006.01)
    *G01N 33/28*     (2006.01)

(52) U.S. Cl.
    CPC .......... B01D 36/006 (2013.01); F16K 37/005 (2013.01); *B01D 2201/12* (2013.01); *B01D 2201/167* (2013.01); *B01D 2201/291* (2013.01); *B01D 2201/316* (2013.01); *G01N 33/2847* (2013.01)

(58) Field of Classification Search
    CPC .... B01D 29/605; B01D 29/60; B01D 35/301; B01D 35/30; B01D 2201/12; B01D 2201/167; B01D 2201/291; B01D 2201/316; B01D 2201/34; G01N 33/2847; F16K 37/005; F16K 37/00
    USPC ........................................................ 210/117
    See application file for complete search history.

(56) References Cited

U.S. PATENT DOCUMENTS

| | | | | |
|---|---|---|---|---|
| 2006/0180537 A1* | 8/2006 | Loftis | .................... | B01D 27/00 |
| | | | | 210/209 |
| 2014/0061110 A1* | 3/2014 | Hawkins | ................ | B01D 27/06 |
| | | | | 210/232 |

OTHER PUBLICATIONS

International Search Report and Written Opinion issued for International Application No. PCT/US2017/060781, dated Jan. 18, 2018, 13 pages.

* cited by examiner

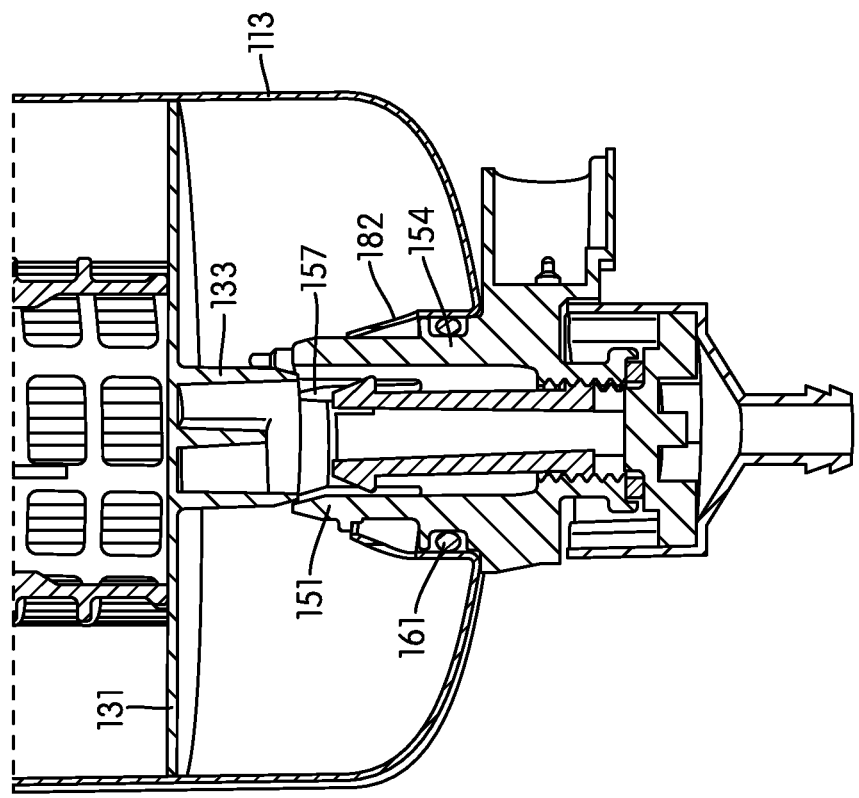
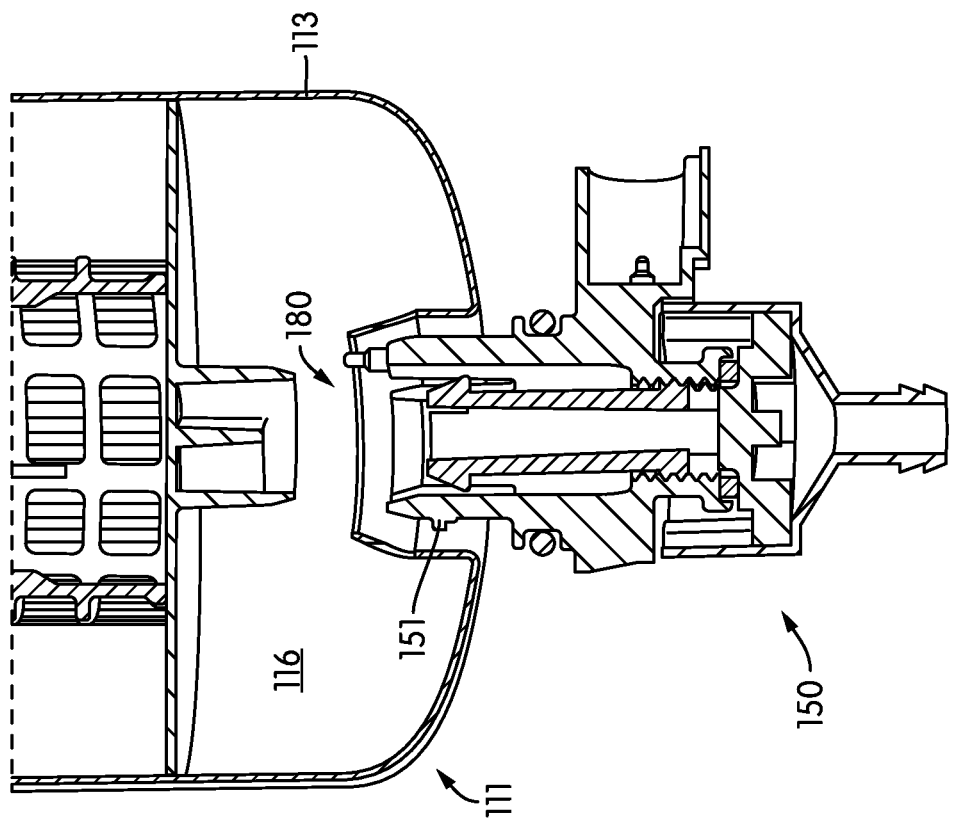

VALVE-SENSOR ASSEMBLY

CROSS REFERENCE TO RELATED APPLICATIONS

This application is a national stage of PCT Application No. PCT/US2017/060781, filed Nov. 9, 2017 which claims priority to and the benefit of U.S. Provisional Application No. 62/429,266 filed Dec. 2, 2016 and entitled "Valve-Sensor Assembly". The contents of both applications are incorporated herein by reference in their entirety.

FIELD

The present application relates generally to fluid filtration systems. More particularly, the present application relates to filter assemblies having water sensors and drain valve systems.

BACKGROUND

In motor vehicles, filtration systems may be provided that separate water from a fluid, such as a fuel, before the fluid is introduced into the engine. The filtration systems may include a water sensor (often referred to as a "water-in-fuel sensor" in fuel filtration systems or a "water-in-fluid sensor" more generally) that extends into an interior of the filtration system to detect a fluid level of the water that has been separated from the fluid and collected within the filtration system. The filtration systems may also include a drain valve that is opened when the sensor detects that the fluid level of the water has reached a predetermined level.

Often, the water sensor is provided separately from the drain valve. During servicing, the water sensor and the drain valve are manually removed and installed independently (via, for example, threaded, nut, or screw connections), increasing servicing costs. In addition, when servicing the water sensor, the plug that electrically connects the sensor to an external power and control system must be disconnected prior to removing the water sensor because the sensor must be rotated to remove the sensor from the system. During installation, the sensor is installed in place before the plug is re-connected. This type of servicing increases the amount of wear to the plug due to the connection-disconnection process and the potential of misalignment between the plug and the sensor during installation, thereby increasing the risk of plug failure.

SUMMARY

A first set of embodiments provide for a valve-sensor assembly for a filter assembly that filters water from a fluid. The valve-sensor assembly comprises a sensor body and a drain valve body. The sensor body comprises a filter element engagement portion having a hollow interior that extends longitudinally through a length of the sensor body and a protrusion that extends circumferentially along an exterior surface of the filter element engagement portion. The sensor body further comprises one or more water-in-fluid sensors provided at the exterior surface of the filter element engagement portion. The drain valve body comprises a main body having a drain port, and a valve extending from the main body and extending at least partially within the hollow interior. The valve has an interior passage in fluid communication with the drain port.

A second set of embodiments provide for a filter system for filtering a fluid. The filter system comprises a housing, a filter element, and a valve-sensor assembly. The housing comprises a bottom portion defining an interior space and comprising a sleeve extending from a bottom surface into the interior space and defining an opening. The filter element is provided within the housing and comprises an endcap provided at one end of the filter element. The endcap comprises a sleeve attachment that extends into the interior space of the bottom portion. The valve-sensor assembly comprises a sensor body and a drain valve body. The sensor body comprises a filter element engagement portion having a hollow interior that extends longitudinally through a length of the sensor body and a protrusion that extends circumferentially along an exterior surface of the filter element engagement portion. The sensor body further comprises one or more water-in-fluid sensors provided at the exterior surface of the filter element engagement portion. The drain valve body comprises a main body having a drain port, and a valve extending from the main body and extending at least partially within the hollow interior. The valve has an interior passage in fluid communication with the drain port. In an installed position of the valve-sensor assembly, the filter element engagement portion extends through the opening of the sleeve, the sleeve attachment extends into the hollow interior of the filter element engagement portion, and the protrusion extends over a top end of the sleeve of the bottom portion such that the valve-sensor assembly detachably connects to the housing.

A third set of embodiments provide for a filter assembly comprising a housing and a valve-sensor assembly. The housing comprises a bottom portion defining an interior space and comprising a sleeve extending from a bottom surface into the interior space. The sleeve defines an opening. The valve-sensor assembly comprises a sensor body and a drain valve body. The sensor body comprises a filter element engagement portion having a hollow interior that extends longitudinally through a length of the sensor body and a protrusion that extends circumferentially along an exterior surface of the filter element engagement portion. The sensor body further comprises one or more water-in-fluid sensors provided at the exterior surface of the filter element engagement portion. The drain valve body comprises a main body having a drain port, and a valve extending from the main body and extending at least partially within the hollow interior. The valve has an interior passage in fluid communication with the drain port. In an installed position of the valve-sensor assembly, the filter element engagement portion extends through the opening of the sleeve, and the protrusion extends over a top end of the sleeve of the bottom portion such that the valve-sensor assembly detachably connects to the housing.

These and other features, together with the organization and manner of operation thereof, will become apparent from the following detailed description when taken in conjunction with the accompanying drawings, wherein like elements have like numerals throughout the several drawings described below. It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

The foregoing and other features of the present disclosure will become more fully apparent from the following description and appended claims taken in conjunction with the accompanying drawings. Understanding that these drawings depict only several implementations in accordance with the disclosure and are therefore not to be considered limiting of its scope, the disclosure will be described with additional specificity and detail through use of the accompanying drawings.

FIG. 5A is a detailed cross-sectional view of the filter system during installation of the valve combination with element interface at a first position.

FIG. 5B is a detailed cross-sectional view of the filter system during installation of the valve combination with element interface at a second position.

Figure 1B:
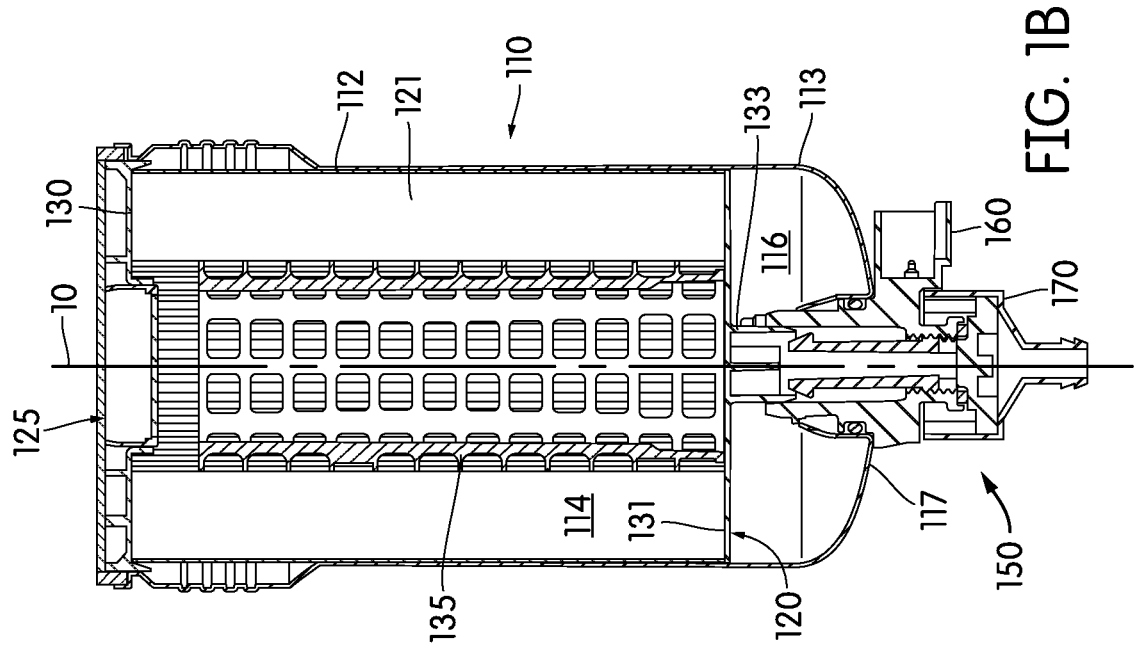
FIG. 1B is a cross-sectional view of the filter system of FIG. 1A.

Reference is made to the accompanying drawings throughout the following detailed description. In the drawings, similar symbols typically identify similar components unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Various example embodiments provide for a filter system having a valve-sensor assembly that includes a filter element interface capable of detachably engaging a housing of the filter system and a filter element provided within the housing. When installed, the filter element interface allows the valve-sensor assembly to be rotated by a user to a desired position for optimal connection positions and/or servicing. In addition, the filter element interface allows for easy detachment from the filter system through an applied downward force, allowing any external connectors (such as plug extensions for electrical connection of the sensor to an external source) to remain in place even during removal and/or installation.

Figure 1A:
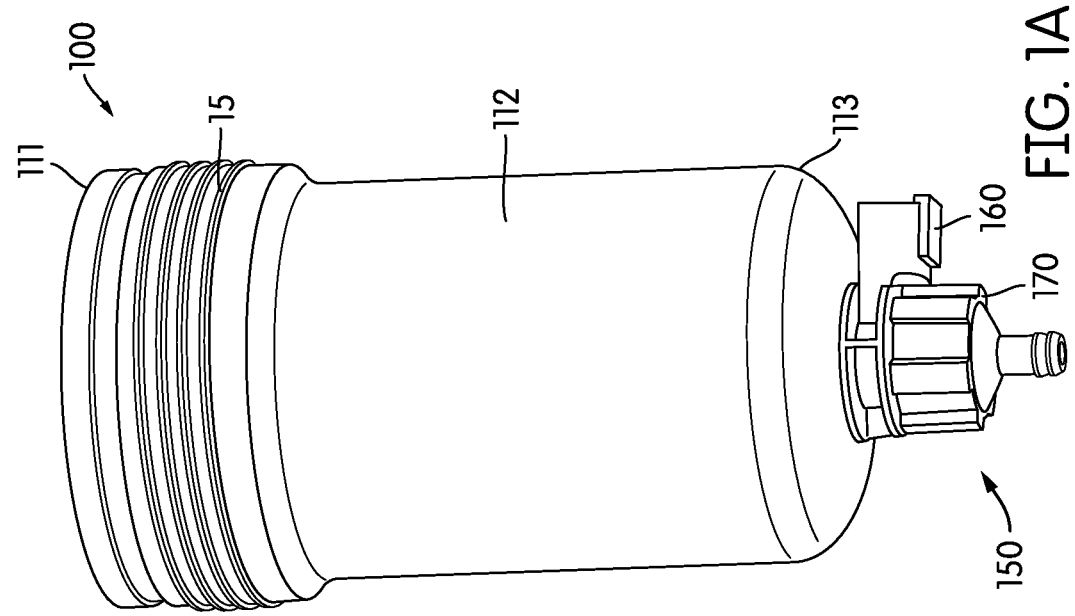
FIG. 1A is a perspective view of a filter system having a valve combination with element interface according to an example embodiment.

FIGS. 1A and 1B show a filter system 100 having a valve-sensor assembly with filter element interface according to an example embodiment. As shown in the figures, the filter system 100 generally includes a filter assembly 110 and a valve-sensor assembly 150.

The filter assembly 110 includes a housing or shell 111 having a body portion 112 and a bottom portion 113 provided at a bottom of the body portion 112. As shown in FIGS. 1A and 1B, the body portion 112 of the housing 111 includes threads 15 configured to engage with a lid or cover (not shown) or other form of attachment to a system that permits fluid for filtering to enter into and/or exit the filter system 100. As shown in FIG. 1B, positioned within an interior space 114 of the body portion 112 is a filter element or cartridge 120, which is configured to filter water from the fluid entering into the filter system 100. In one example embodiment, the filter element 120 is configured to filter water from a fuel. However, in other embodiments, the filter element 120 may be used to filter other types of fluid, such as oil, lube, or the like. The filter element 120 includes a filter media 121, a first end cap 130 attached to a first end of the filter media 121, and a second end cap 131 attached to a second end of the filter media 121.

In the embodiment shown in the figures, the filter media 121 is substantially cylindrical in shape and includes an inner annulus 125 that extends along a central longitudinal axis 10 of the filter element 120. The filter media 121 may include any configuration for filtering water from a fluid, including, but not limited to, a pleated configuration. Disposed within the inner annulus 125 may be a standpipe 135, which may be configured to provide internal support to the filter media 121.

As further shown in FIG. 1B, the bottom portion 113 of the housing 111 is formed as a bowl-like shape and includes an interior space 116. In an example embodiment, the bottom portion 113 is configured to receive water that has been filtered from the fluid within the interior space 116. The bottom portion 113 is further configured to receive within the interior space 116 the valve-sensor assembly 150 through a bottom surface 117 of the housing 111. In addition, the second end cap 131 includes a sleeve attachment 133 that extends downwardly from the second end cap 131 along the central longitudinal axis 10 into the interior space 116. The sleeve attachment 133 is configured to attach to the valve-sensor assembly 150, which is described in more detail below.

Figure 2B:
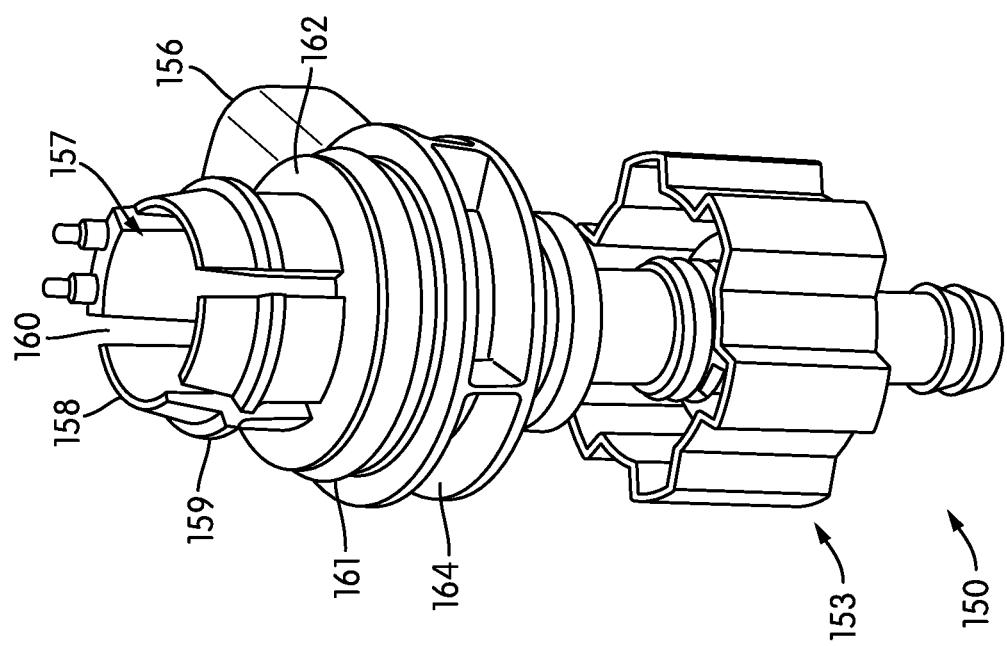
FIG. 2B is a detailed, perspective view of an open position of the valve combination with element interface of FIG. 1A.
Figure 2A:
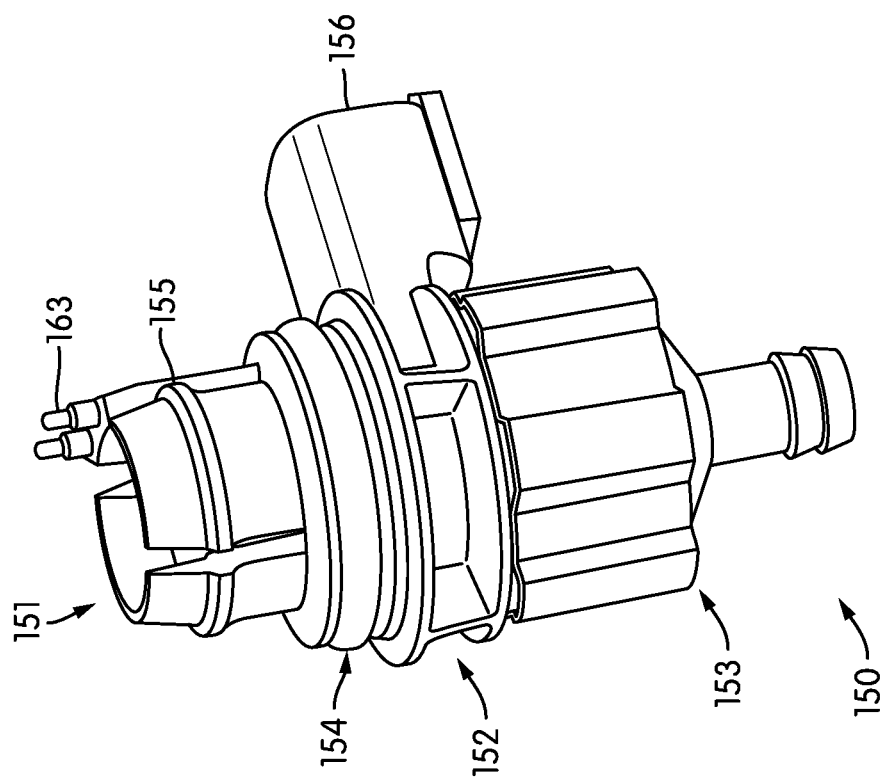
FIG. 2A is a detailed, perspective view of a closed position of the valve combination with element interface of FIG. 1A.

FIGS. 2A and 2B show detailed, perspective views of the valve-sensor assembly 150 according to an example embodiment. As shown in FIGS. 2A and 2B, the valve-sensor assembly 150 includes a sensor body 152 and a drain valve body 153. The sensor body 152 is configured to detachably connect in a sealing arrangement to the bottom portion 113 of the housing 111 and the sleeve attachment 133 of the second end cap 131. In addition, the sensor body 152 of the valve-sensor assembly 150 includes a filter element engagement portion 151, a sensor portion 155, a sealing portion 154, and an external connection portion 156.

The filter element engagement portion 151 is configured to engage with the sleeve attachment 133 of the second end cap 131 of the filter element 120. As shown in FIGS. 2A and 2B, the filter element engagement portion 151 extends upward (i.e., towards the filter element 120 when the valve-sensor assembly 150 is installed) from the sealing portion 154. As shown in FIG. 2B, the filter element engagement portion 151 includes a connection body 158 that connects to the sleeve attachment 133. The connection body 158 is generally cylindrical in shape and includes a hollow interior 157 that extends longitudinally through the length of the sensor body 152 and receives a portion of the drain valve body 153 (see FIGS. 3A and 3B). As will be described further below, the hollow interior 157 is also configured to receive the sleeve attachment 133 such that the connection body 158 engages with the sleeve attachment 133.

Extending circumferentially along an exterior surface of the connection body 158 is a protrusion or lip 159, which extends radially outward relative to the connection body 158 to form a circumferential ridge. As will be further described below, the protrusion 159 is configured to detachably engage with the bottom portion 113 of the housing 111. As shown in FIG. 2B, the connection body 158 may be further provided with a plurality of longitudinally extending cutouts 160 such that the connection body 158 comprises a plurality of deflective protrusions or fingers. For example, as shown in FIG. 2B, the connection body 158 may include four cutouts 160 such that the connection body 158 includes four deflective fingers. As will be described in more detail below, the deflective protrusions are configured to deflect or deform to allow the filter element engagement portion 151 to engage with the sleeve attachment 133 upon installation of the valve-sensor assembly 150. In addition, the cutouts 160 also provide flow passages for water during draining of the bottom portion 113 of the housing 111.

As shown in FIG. 2A, the sensor portion 155 includes one or more sensors 163 provided on the exterior surface of the connection body 158. The sensors 163 extend upward from the sealing portion 154 and along the exterior surface of the connection body 158. The sensors 163 may be provided separately from the connection body 158 or may be integrally formed with the connection body 158. In an example embodiment, the sensors 163 are water-in-fluid sensors that are configured to detect a level of water present in the filter fluid collected in the interior space 116 of the bottom portion 113 of the housing 111. In an additional example embodiment, the sensors 163 are water-in-fuel sensors. The sensors 163 are configured to electrically connect to a plug extension that is received within the external connection portion 156.

The sealing portion 154 is configured to sealingly engage with the bottom portion 113 of the housing 111. As shown in FIG. 2B, the sealing portion 154 includes an upper portion 162 from which the filter element engagement portion 151 and the sensor portion 155 extend and a lower portion 164 from which the external connection portion 156 extends. The upper portion 162 and the lower portion 164 form a circumferential depression or notch therebetween, which is configured to receive a sealing element 161, such an O-ring, for sealing engagement with the housing 111 of the filter assembly 110 upon installation of the valve-sensor assembly 150.

The external connection portion 156 extends radially outward from an exterior side of the lower portion 164 of the sealing portion 154. The external connection portion 156 defines an interior space 165 (see FIGS. 3A and 3B) that is configured to receive a plug extension for electrical connection of the valve-sensor assembly 150 to an external source, such as an engine control unit. The external connection portion 156 further includes a connector 166 (see FIGS. 3A and 3B) that extends radially out from the lower portion 164 of the sealing portion 154 within the interior space 165. The connector 166 is configured to connect to the plug extension such that an electrical connection is established between the sensors 163 and the external source.

Figure 3B:
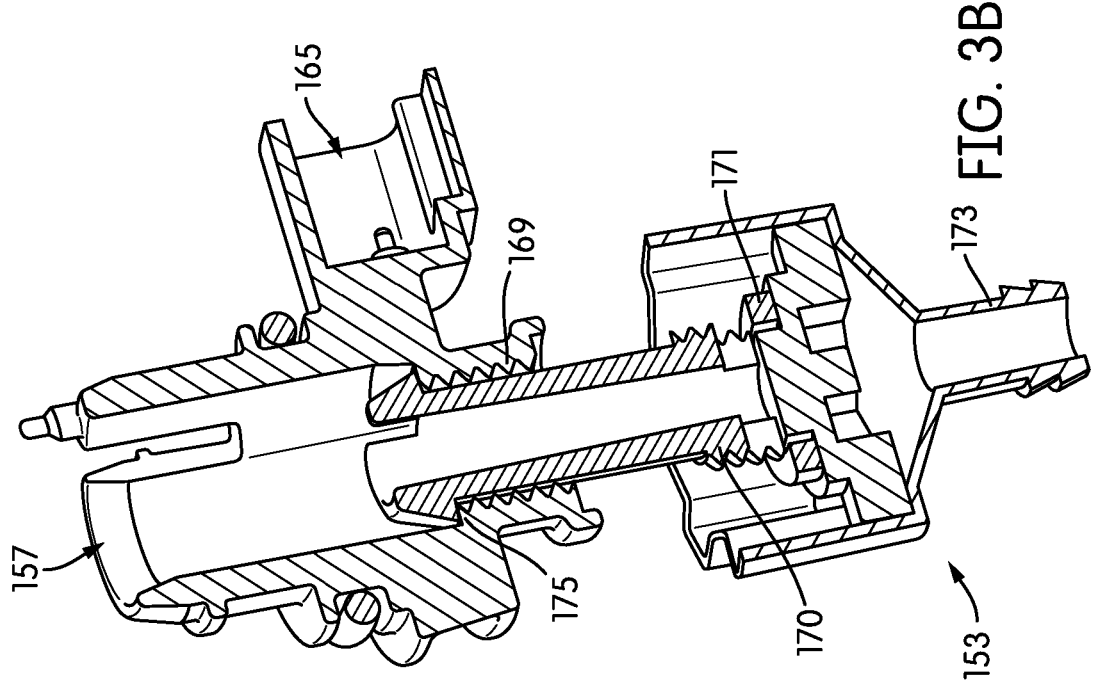
FIG. 3B is a detailed, cross-sectional view of the open position of the valve combination with element interface of FIG. 2B.
Figure 3A:
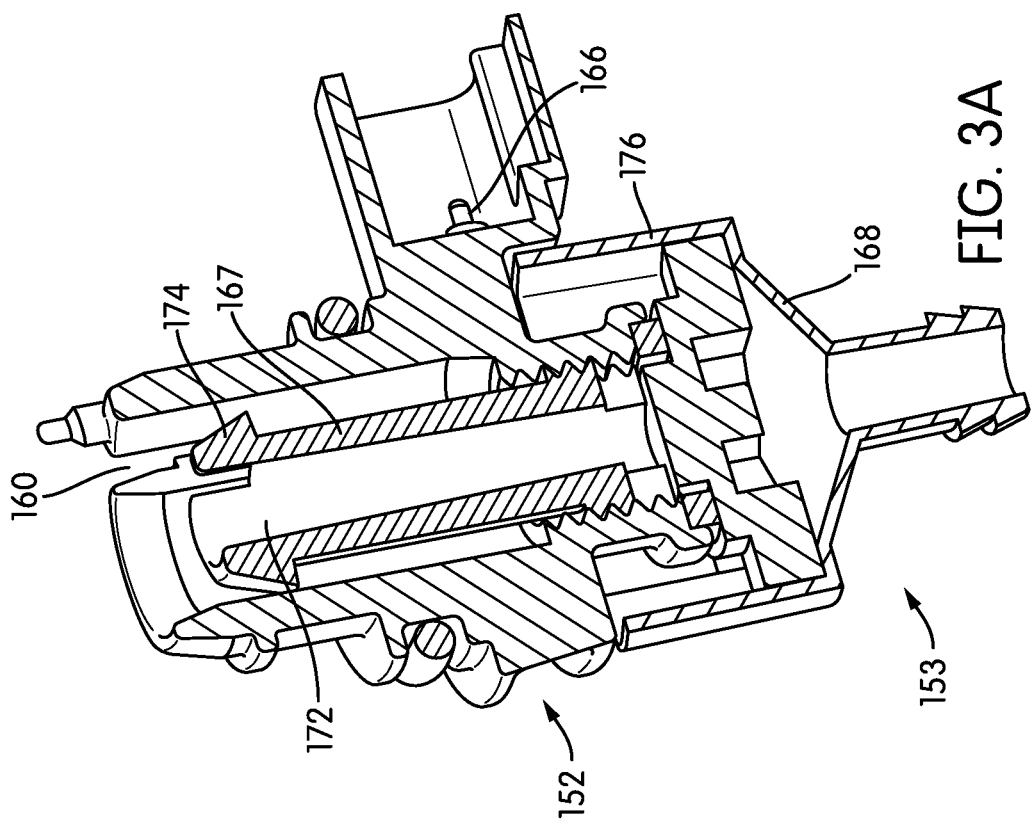
FIG. 3A is a detailed, cross-sectional view of the closed position of the valve combination with element interface of FIG. 2A.

FIGS. 3A and 3B show detailed cross-sectional views of the valve-sensor assembly 150. FIG. 3A shows a detailed cross-sectional view of the valve-sensor assembly 150 when the drain valve body 153 is in a closed position. FIG. 3B shows a detailed cross-sectional view of the valve-sensor assembly 150 when the drain valve body 153 is in an open position.

As shown in FIGS. 3A and 3B, the drain valve body 153 includes a valve 167 and a main body 168. The valve 167 extends upward from the main body 168 and into the hollow interior 157 of the sensor body 152. The valve 167 includes a longitudinally extending interior passage 172 that forms a flow passage within the valve 167 for water flow. At a bottom portion of the valve 167, threads 170 are provided that are configured to engage mating threads 169 provided on an interior surface of the hollow interior 157 of the sensor body 152 when the drain valve body 153 is in the closed position, as shown in FIG. 3A. At a bottom end of the valve 167 is a sealing element 171, such as, for example, an O-ring, which sealingly engages with a bottom of the sensor body 152. At a top portion of the valve 167 is an outwardly extending protrusion 174. The protrusion 174 is configured to contact a shoulder 175 provided in the hollow interior 157 to prevent the drain valve body 153 from becoming detached from the sensor body 152 when the drain valve body 153 is in the open position, as shown in FIG. 3B.

As further shown in FIGS. 3A and 3B, the main body 168 includes an upper portion 176 that is configured to receive and circumferentially surround a bottom portion of the sensor body 152 when the drain valve body 153 is in the closed position. Extending downward from the upper portion 176 is a drain port 173 configured to connect to a conduit to allow water to drain externally from the filter system 100.

When the sensors 163 detect that the water level within the bottom portion 113 of the housing 111 has reached a predetermined level, the sensors 163, via its electrical connection(s) to the external source, may be configured to alert the user of a need to drain the filter assembly 110. The user may then rotate the drain valve body 153 relative to the sensor body 152 and move the drain valve body 153 from the closed position to the open position such that the threads 170 disengage from the mating threads 169 of the sensor body 152. By moving the drain valve body 153 to the open position, water may quickly drain from the bottom portion 113 of the housing 111 through the cutouts 160 of the sensor body 152 and the interior passage 172 of the valve 167, which is in fluid communication with the interior of the main body 168 and the drain port 173, allowing water to exit from the filter system 100. Although the example embodiment shown in FIGS. 3A and 3B show a drain valve body 153 that is manually opened to allow for quick drainage of the filter system 100, the drain valve body 153 may be automatically opened in other embodiments. In embodiments where the drain valve body 153 is opened automatically, the external connection portion 156 may be further configured to allow for electrical connection of the drain valve body 153 to the external source.

Figure 4:
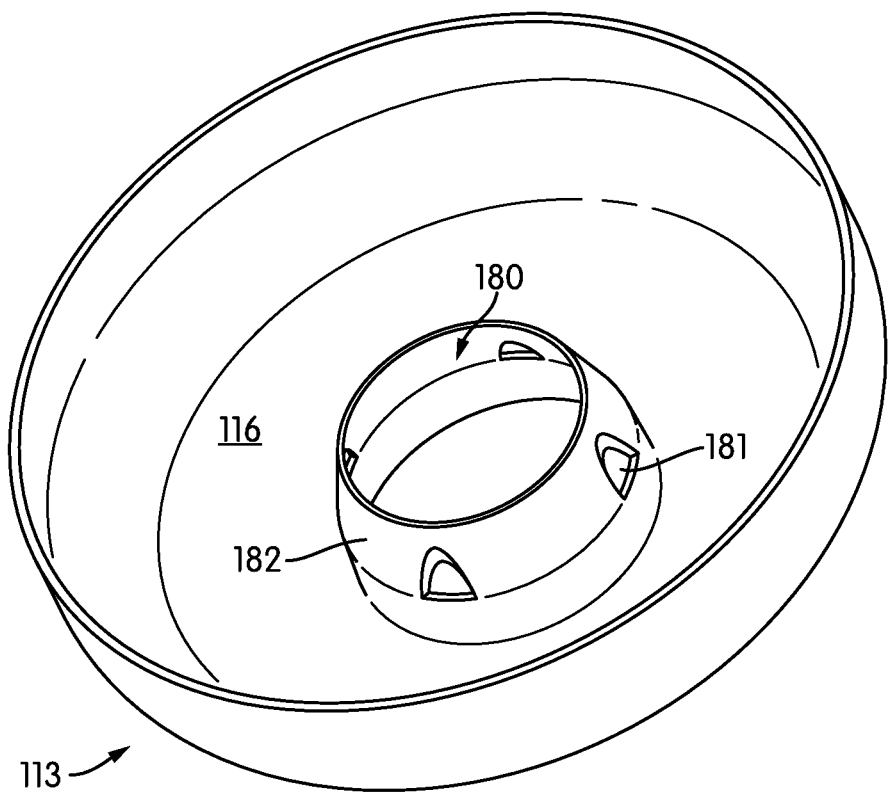
FIG. 4 is a detailed, perspective view of a bowl portion of the filter system of FIG. 1A.

FIG. 4 shows a cross-sectional perspective view of the bottom portion 113 of the housing 111. The bottom portion 113 includes a sleeve 182, which is provided at a center portion of the bottom surface 117 of the bottom portion 113 and extends upward from the bottom surface 117. The sleeve 182 defines an opening 180. As shown in FIG. 4, a top portion of the sleeve 182 extends at an inward angle relative to a bottom portion of the sleeve 182 such that a diameter of the opening 180 at a bottom end of the sleeve 182 is greater than a diameter of the opening 180 at a top end of the sleeve 182. The opening 180 and the sleeve 182 are configured to receive the filter element engagement portion 151 when the valve-sensor assembly 150 is installed. Flow passages in the form of one or more fluid openings 181 are provided in the wall of the sleeve 182 to allow for water flow from the bottom portion 113 during draining.

Figure 5C:
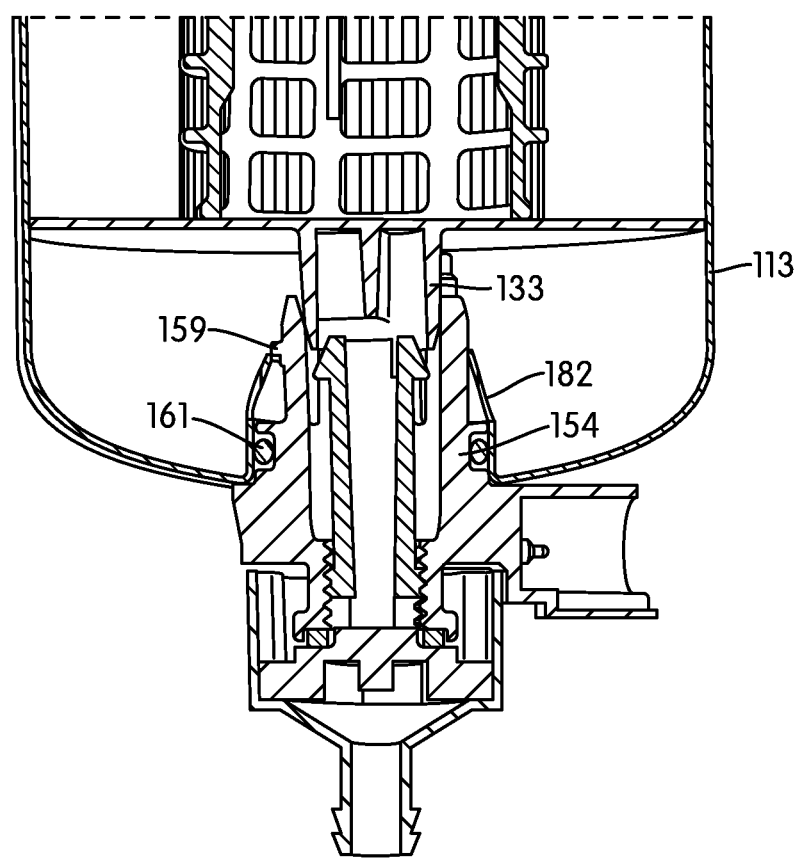
FIG. 5C is a detailed cross-sectional view of the filter system during installation of the valve combination with element interface at a third position.

FIGS. 5A-5C show detailed cross-sectional views of the filter system 100 during installation of the valve-sensor assembly 150. As shown in FIG. 5A, the filter element engagement portion 151 of the valve-sensor assembly 150 is received within the opening 180 of the bottom portion 113 of the housing 111. The valve-sensor assembly 150 is moved upward into the interior space 116 of the bottom portion 113 towards the sleeve attachment 133 of the second end cap 131. As shown in FIG. 5B, when the valve-sensor assembly 150 approaches the sleeve attachment 133, the sleeve attachment 133 is partially received within the hollow interior 157 of the filter element engagement portion 151. At this point, the sealing element 161 sealingly engages with an interior surface of the sleeve 182 of the bottom portion 113.

As the valve-sensor assembly 150 is moved further towards the second end cap 131, the sleeve attachment 133 is further received within the hollow interior 157 of the filter element engagement portion 151. As shown in FIG. 5C, the sleeve attachment 133 causes the filter element engagement portion 151 to deflect or deform radially outward such that the protrusion 159 extends over the sleeve 182 and an underside of the protrusion 159 contacts a top end of the sleeve 182 of the bottom portion 113, which detachably connects (or removably attaches) and installs the valve-sensor assembly 150 to the bottom portion 113. The connection of the valve-sensor assembly 150 to the bottom portion 113 and sleeve attachment 133 allows the valve-sensor assembly 150 to be rotated without being detached from the filter assembly 110. This rotation allows a user to rotate the valve-sensor assembly 150 after installation to a desired position, such as a position that aligns the external connection portion 156 with the plug extension.

To remove the valve-sensor assembly 150 from the filter assembly 110, the user applies a downward force to the valve-sensor assembly 150. Because the protrusion 159 connecting the valve-sensor assembly 150 to the sleeve 182 extends outwardly over a short distance and because the filter element engagement portion 151 deflects inward as the sleeve attachment 133 moves out from the hollow interior 157, the force required to disengage the valve-sensor assembly 150 from the housing 111 is small. Moreover, because the user only needs to apply a downward force to remove the valve-sensor assembly 150, rather than, for example, rotating the assembly, the plug extension may remain installed within the external connection portion 156 during removal of the valve-sensor assembly 150, thereby reducing the risk of wear to the plug extension. In addition, while the embodiments shown in the figures include a valve-sensor assembly 150 configured to receive a plug extension, other embodiments of the valve-sensor assembly 150 may eliminate the need of a plug extension by including an integrated wiring harness rather than an external connection portion 156.

The term "connected" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the various example embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, various parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various example embodiments without departing from the scope of the concepts presented herein.

While this specification contains many specific implementation details, these should not be construed as limitations on the scope of any embodiments or of what may be claimed, but rather as descriptions of features specific to particular implementations of particular embodiments. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A valve-sensor assembly for a filter assembly that filters water from a fluid, the valve-sensor assembly comprising:
   a sensor body comprising:
      a filter element engagement portion having a hollow interior that extends longitudinally through a length of the sensor body, and a protrusion that extends circumferentially along an exterior surface of the filter element engagement portion; and
      one or more water-in-fluid sensors provided at the exterior surface of the filter element engagement portion; and
   a drain valve body comprising:
      a main body having a drain port; and
      a valve extending from the main body and extending at least partially within the hollow interior, the valve having an interior passage in fluid communication with the drain port.

2. The valve-sensor assembly of claim 1, wherein the one or more water-in-fluid sensors comprises a plurality of water-in-fluid sensors.

3. The valve-sensor assembly of claim 1, wherein the filter element engagement portion further comprises a connection body, the connection body provided with a plurality of longitudinal extending cutouts such that the connection body comprises a plurality of deflective protrusions.

4. The valve-sensor assembly of claim 3, wherein the plurality of deflective protrusions are configured to at least one of deflect to allow the filter element engagement portion to engage with a filter element and provide flow passages for water.

5. The valve-sensor assembly of claim 1, wherein the sensor body further comprises a sensor portion, the one or more water-in-fluid sensors provided in the sensor portion.

6. The valve-sensor assembly of claim 5, wherein the sensor body further comprises a sealing portion, the sealing portion comprising an upper portion and a lower portion, wherein the filter element engagement portion and the sensor portion extend upward from the upper portion.

7. The valve-sensor assembly of claim 6, wherein the sensor body further comprises an external connection portion, the external connection portion defining an interior space configured to receive a plug extension for electrical connection of the valve-sensor assembly to an external source.

8. The valve-sensor assembly of claim 7, wherein the external connection portion extends radially outwards from an exterior side of the lower portion of the sealing portion.

9. The valve-sensor assembly of claim 6, wherein the upper portion and the lower portion form a circumferential depression therebetween, the circumferential depression structured to receive a sealing element.

10. The valve-sensor assembly of claim 1, wherein a shoulder is provided in the hollow interior, and wherein the valve comprises a top portion and a bottom portion, an outwardly extending protrusion provided on the top portion of the valve, the outwardly extending protrusion configured to contact the shoulder so as to prevent the drain valve body from becoming detached from the sensor body when the drain valve body is in an open position.

11. The valve-sensor assembly of claim 10, wherein the bottom portion of the valve comprises threads configured to engage mating threads provided on an interior surface of the hollow interior when the drain valve body is in a closed position, and wherein the drain valve body is movable from the closed position into the open position by rotating the drain valve body relative to the sensor body, the threads disengaging from the mating threads in the open position.

12. The valve-sensor assembly of claim 1, wherein the main body comprises an upper portion configured to receive and circumferentially surround a bottom portion of the sensor body when the drain valve body is in a closed position.

13. A filter system for filtering a fluid, the filter system comprising:
   a housing having a bottom portion, the bottom portion defining an interior space and comprising a sleeve extending from a bottom surface into the interior space, the sleeve defining an opening;
   a filter element provided within the housing and having an endcap provided at one end of the filter element, the endcap comprising a sleeve attachment extending into the interior space; and
   a valve-sensor assembly comprising:
      a sensor body comprising:
         a filter element engagement portion having a hollow interior that extends longitudinally through a length of the sensor body and a protrusion that extends circumferentially along an exterior surface of the filter element engagement portion; and
         one or more water-in-fluid sensors provided at the exterior surface of the filter element engagement portion; and
      a drain valve body comprising:
         a main body having a drain port; and
         a valve extending from the main body and extending at least partially within the hollow interior, the valve having an interior passage in fluid communication with the drain port,
   wherein in an installed position of the valve-sensor assembly:
      the filter element engagement portion extends through the opening of the sleeve,
      the sleeve attachment extends into the hollow interior of the filter element engagement portion, and
      the protrusion extends over a top end of the sleeve of the bottom portion such that the valve-sensor assembly detachably connects to the housing.

14. The filter system of claim 13, wherein the one or more water-in-fluid sensors comprises a plurality of water-in-fluid sensors.

15. The filter system of claim 13, wherein one or more fluid openings are provided in the sleeve, the one or more fluid openings configured to allow water to flow from the bottom portion during draining of the filter system.

16. The filter system of claim 13, wherein the sleeve attachment is structured to cause the filter element engagement portion to deflect radially outward such that the protrusion extends over the top end of the sleeve of the bottom portion.

17. The filter system of claim 13, wherein a shoulder is provided in the hollow interior, and wherein the valve comprises a top portion and a bottom portion, an outwardly extending protrusion provided on the top portion of the valve, the outwardly extending protrusion configured to contact the shoulder to prevent the drain valve body from becoming detached from the sensor body when the drain valve body is in an open position.

18. The filter system of claim 17, wherein the bottom portion of the valve comprises threads configured to engage mating threads provided on an interior surface of the hollow interior when the drain valve body is in a closed position, and wherein the drain valve body is movable from the closed position into the open position by rotating the drain valve body relative to the sensor body, the threads disengaging from the mating threads in the open position.

19. The filter system of claim 13, wherein the main body comprises an upper portion configured to receive and circumferentially surround a bottom portion of the sensor body when the drain valve body is in a closed position.

20. A filter assembly, comprising:
   a housing having a bottom portion, the bottom portion defining an interior space and comprising a sleeve extending from a bottom surface into the interior space, the sleeve defining an opening; and
   a valve-sensor assembly comprising:
      a sensor body comprising:
         a filter element engagement portion having a hollow interior that extends longitudinally through a length of the sensor body and a protrusion that extends circumferentially along an exterior surface of the filter element engagement portion; and
         one or more water-in-fluid sensors provided at the exterior surface of the filter element engagement portion; and
      a drain valve body comprising:
         a main body having a drain port; and a valve extending from the main body and extending at least partially within the hollow interior, the valve having an interior passage in fluid communication with the drain port, wherein in an installed position of the valve-sensor assembly, the filter element engagement portion extends through the opening of the sleeve, and the protrusion extends over a top end of the sleeve of the bottom portion such that the valve-sensor assembly detachably connects to the housing.

21. The filter assembly of claim 20, wherein one or more fluid openings are provided in the sleeve, the one or more fluid openings configured to allow water to flow from the bottom portion during draining of the filter assembly.

* * * * *